(12) United States Patent
Jones

(10) Patent No.: US 6,258,372 B1
(45) Date of Patent: *Jul. 10, 2001

(54) XYLITOL NOSE SPRAY

(76) Inventor: Alonzo H. Jones, P.O. Box 186, Hale Center, TX (US) 79041

( * ) Notice: Subject to any disclaimer, the term of this patent is extended or adjusted under 35 U.S.C. 154(b) by 0 days.

This patent is subject to a terminal disclaimer.

(21) Appl. No.: 09/517,929

(22) Filed: Mar. 3, 2000

Related U.S. Application Data

(62) Division of application No. 09/220,283, filed on Dec. 23, 1998, now Pat. No. 6,054,143.
(60) Provisional application No. 60/079,184, filed on Mar. 24, 1998.

(51) Int. Cl.⁷ .............................. A61F 13/00; A61K 31/70
(52) U.S. Cl. ................................................ 424/434; 514/23
(58) Field of Search ............................... 424/434; 514/23

(56) References Cited

U.S. PATENT DOCUMENTS

| | | | |
|---|---|---|---|
| 5,719,196 | * | 2/1998 | Uhari et al. ........................... 514/738 |
| 6,054,143 | * | 4/2000 | Jones ..................................... 424/434 |

* cited by examiner

*Primary Examiner*—Kevin E. Weddington
(74) *Attorney, Agent, or Firm*—Wendell Coffee; Mark Scott

(57) ABSTRACT

Nasopharyngeal congestion, irritation, and inflammation and associated upper respiratory infections such a otitis media, sinusitis are adjunctivly treated and prevented by nasal application of xylitol/xylose in a saline solution.

11 Claims, No Drawings

XYLITOL NOSE SPRAY

CROSS REFERENCE TO RELATED APPLICATION

This is a Division of U.S. patent application Ser. No. 09/220,283 filed Dec. 23, 1998, entitled XYLITOL DELIVERY, which is now U.S. Pat. No. 6,054,143 issued on Apr. 25, 2000.

Applicant filed a Provisional Application on this subject matter on Mar. 24, 1998, Ser. No. 60/079,184. Specific reference is made to that document.

BACKGROUND OF THE INVENTION (1) Field of the Invention

This invention relates to cleaning the nasopharynx and thereby reducing the number of bacteria resident there. This reduction translates into less problems with upper respiratory infections (specifically otitis and sinusitis) and reduction in the severity of asthma when the asthma is triggered by upper respiratory irritants. General practice physicians have ordinary skill in this art.

(2) Description of the Related Art

Xylitol is the alcohol form of xylose, a pentose wood sugar. Since both forms are readily interchangeable, the term "xylitol/xylose" is used herein to mean "xylitol" or "xylose" or "xylitol and xylose". Xylitol, xylose, and mixtures of xylitol and xylose are equivalent and all equally effective in equal amounts in all therapeutic uses described herein. Xylitol is present in natural chemical cycles in the body (see Touster, 1974). It has about the same safety and toxicity as table sugar (Jori, 1984). Based on measuring the amount of xylitol in the urine of a group of southern European people who are deficient in an enzyme that assists in its metabolism Touster points out that the human body uses between 5 and 15 grams of xylitol daily. Xylitol is approved by the FDA as a food additive and is widely used as a sweetener especially in chewing gums. Xylitol is available at most health food stores. When ingested by mouth xylitol is about 90% absorbed, mostly in the jejunum, and rapidly metabolized; Asano and his group could find no detectable xylitol in the serum one and two hours after oral doses of 5 to 30 grams (Asano, 1973). Xylose is found in the body on the glycoprotein ligands that extend from cells and that are thought to participate in intercellular communication (Murray, 1996). Xylitol/xylose has been studied extensively for reducing dental caries through its effect on strep mutans, one of the bacterial responsible for cariogenic plaque. These studies have demonstrated that the action of xylitol/xylose that produces the cariogenic protection is by making this bacteria weaker and less adherent to dental plaque (Trahan, 1995). Paul Naaber found a similar decrease in adherence when he looked at Clostridium difficile in the gut in the presence of xylitol/xylose (Naaber, 1996). In 1998 Kontiokari found that a 2.5 percent solution of xylitol/xylose decreased the adherence of this bacteria when present either in the nasal mucosal cell or in the bacteria. When a five percent solution was present in both the bacteria and the mucosal cell, adherence of strep pneumonia, the major pathogen, was reduced by two-thirds; from an average of 41 bacteria per cell to 13 (Kontiokari, 1998). His article concludes by stating:

"These observation are consistent with the fact that monosaccharides are able to inhibit adherence only at the high concentrations, that are easily achieved in the oral cavity. The worldwide spread of penicillin-resistant strains of pneumocci substantiates the need for new approaches to preventing bacterial infections. Xylitol seems to be a promising agent for this purpose."

Matti Uhari, one of Kontiokari's colleagues in Finland has been studying the effects of oral xylitol/xylose in reducing the incidence of recurrent otitis as disclosed in U.S. Pat. No. 5,719,196 (Uhari, 1996; Uhari, 1998). Uhari's original study looks at the effect of xylitol chewing gum in reducing the incidence of otitis. The highest incidence of otitis is in infants less than two who cannot chew gum. Uhari subsequently studied the incidence of otitis in children getting an oral solution of xylitol. He found between a thirty and forty-percent reduction in the incidence of otitis using these supplements.

SUMMARY OF THE INVENTION (1) Progressive Contribution to the Art

The first level of response of the immune system is to try and wash out the irritated area. In upper respiratory infections this usually translates into nasal congestion because the immune system gets the fluid it needs for this washing and dilating blood vessels in the area. The traditional response to these symptoms is to turn off the immune response by a decongestant or antihistamine. A treatment much more respectful of the wisdom of the immune system is to facilitate it in the attempt to wash the irritated area.

I have discovered that the use of xylitol in a saline solution as a nasal spray is a beneficial means for delivering xylitol more efficiently to the nasopharynx. It avoids the dilution associated with ingestion, absorption, metabolism and circulation to the nose where it is active, that is present with oral delivery. Xylitol's effect, even when given orally, is in the nasopharynx. Because of this it is possible to deliver a pleasant nasal spray containing almost three orders of magnitude less than that given orally to accomplish similar results. Use of this spray results in cleaning of the nasopharynx, reduction of the bacterial count in the nasopharynx and a reduction in infections associated with those bacteria. Because the bacteria are not killed, resistance is not as big a problem. The use of this spray as adjunctive treatment of appropriate infections reduces the need for second and third generation antibiotics. "Resistant" strains of strep mutans that can metabolize xylitol have been isolated in the mouth, but they are more friendly and less cariogenic (Trahan, 1995). Use of this cleansing solution translates into less otitis and sinusitis. Where asthma is triggered by upper respiratory inflammation, an amelioration of the severity of the asthma is accomplished. The addition of xylitol/xylose to conventional nasal sprays is an efficient method of administration. It is particularly useful with infants younger than two years who cannot chew gum.

(2) Objects of this Invention

An object of this invention is to reduce infections of the nasopharynx and symptoms associated with these infections.

Another object of this invention is to provide a means to clean the nasopharynx and reduce the population of the pathogenic bacterial resident there.

A further object of this invention is to reduce otitis, sinusitis and, where asthma is triggered by inflammation of the upper airway, a reduction in the severity of asthma.

Another object of this invention is to efficiently deliver xylitol/xylose for the adjunctive treatment of nasopharyngeal infections.

Other objects are to achieve the above with a method that is rapid, effective, efficient, natural, safe, and inexpensive, and does not require highly skilled people to formulate and administer.

Further objects are to achieve the above with a product that has a long storage life, is safe, versatile, efficient, stable and reliable, yet is inexpensive and easy to formulate and administer.

The specific nature of the invention, as well as other objects, uses, and advantages thereof, will clearly appear from the following description.

DESCRIPTION OF THE PREFERRED EMBODIMENTS

A nasal spray is formulated having approximately 10% xylitol/xylose in an aqueous solution. The spray is administered by a conventional spray bottle.

As little as 1% xylitol/xylose in solution appears to be the effective minimum strength, the maximum strength is a saturated solution of 64 grams of xylitol/xylose per 100 cc.s of solution.

Mixing in a saline aqueous solution to facilitate one washing effect of the saline, the saline solution should be slightly hypotonic. The preferred saline solution is a 0.65% sodium chloride solution. The saline solution can be in the range from 0.45% sodium salt to 0.95% sodium salt. More than 0.95% sodium salt results in a burning sensation in the nasal passages. Sodium chloride is the preferred salt to make the saline solution although other compatible sodium compounds may be used.

Therefore it may be seen that nasal application of xylitol/xylose in a saline solution loosens the bacterial attachment and washes the nasal cavity.

One formulation is 5 grams of xylitol/xylose mixed with 45 cubic centimeters of "Ocean" nasal spray manufactured by the Fleming Company of Fenton, Mo. the "Ocean" spray contains 0.65% sodium chloride in water with benzalkonium chloride and phenylcarbinol as preservatives.

The recommended dosage for infants under two is a spray in each nostril with each diaper change. This, also, could be expressed by administering two sprays of the solution about seven times a day. Each spray will deliver approximately five (5) milligrams per spray. With two sprays, seven times a day this would be approximately 70 milligrams per day.

An alternate of application is that the xylitol/xylose solution could be administered as drops from a dropper. If the solution were administered by drops, there would be approximately five (5) milligrams per drop, therefore, a recommended dosage by drops would be two drops in each nostril seven times a day would result in about 140 milligrams per day. About 0.1 gram a day is normally sufficient. Basically, an excess amount is not harmful.

Another form of deliver is by swab, such as cotton wound around a small stick. The swab might be dipped into a xylitol/xylose solution as described above. A stronger solution such as a 25% xylitol/xylose solution is desirable. Also, the xylitol/xylose may be mixed in a carrier other than a solution, such as a suitable gel.

This treatment is beneficial for nasal congestion. Usage as described results in a reduction of the population of resident pathogenic strep pneumonia and other bacteria with similar reduction in infections and inflammatory problems associated with these bacteria. This usage will result in a reduced incident of ear infections. Also, the dosage is recommended to lessen the frequency and severity of recurrent sinus infections.

Also, use of xylitol/xylose, as described above, in combination with a first line antibiotic is usually sufficient for treatment of most upper respiratory conditions where strep pneumonia is the agent involved with the infection.

The embodiment shown and described above is only exemplary. I do not claim to have invented all the parts, elements or steps described. Various modifications can be made in the construction, material, arrangement, and operation, and still be within the scope of my invention. For example, the treatment is beneficial to many people over two years of age.

The restrictive description of the specific examples above do not point out what an infringement of this patent would be, but are to point out the advantages and the progressive contribution to the healing arts and to enable one skilled in the art to make and use the invention. The limits of the invention and the bounds of the patent protection are measured by and defined in the following claims.

I claim as my invention:

1. An aqueous solution for nasal use comprising by weight 100 parts of water, between 65 parts to 1 part of xylitol/xylose, and between 0.95 and 0.45 parts of sodium chloride.

2. The solution as defined in claim 1 with the addition of effective amounts of benzalkonium chloride and phenylcarbinol as preservatives.

3. The solution as defined in claim 2 comprising: 100 parts of water, 10 parts of xylitol/xylose, and 0.65 parts of sodium chloride.

4. The solution as defined in claim 1 wherein the solution is hypotonic and further comprising 100 parts of water, 10 parts of xylitol/xylose, 0.65 parts of sodium chloride and effective amounts of benzalkonium chloride and phenylcarbinol as preservatives.

5. An aqueous solution for nasal use comprising by weight 100 parts of water and between 65 parts to 1 part of xylitol/xylose.

6. The solution as defined in claim 5 with the addition of effective amounts of benzalkonium chloride and phenylcarbinol as preservatives.

7. The solution as defined in claim 6 comprising: 100 parts of water and 10 parts of xylitol/xylose.

8. The solution as defined in claim 5 wherein the solution is hypotonic and further comprising 100 parts of water, 10 parts of xylitol/xylose, and effective amounts of benzalkonium chloride and phenylcarbinol as preservatives.

9. A nasal spray comprising by weight 100 parts of water, between one part and 65 parts of xylitol/xylose, and between 0.45 and 0.95 parts of sodium chloride in a conventional spray bottle.

10. The product as defined in claim 9 wherein said solution is hypotonic and further comprising 100 parts of water 10 parts of xylitol/xylose, and 0.65 parts of sodium chloride and effective amounts of benzalkonium chloride and phenylcarbinol as preservatives.

11. A preparation for nasal use comprising an effective amount of xylitol/xylose in a suitable gel.

* * * * *